United States Patent
Stochniol et al.

(10) Patent No.: US 7,030,052 B2
(45) Date of Patent: Apr. 18, 2006

(54) PROCESS FOR HYDROGENATING AN AROMATIC AMINE IN THE PRESENCE OF A SUPPORTED RUTHENIUM CATALYST

(75) Inventors: Guido Stochniol, Gelnhausen (DE); Bernd Jaeger, Darmstadt (DE); Thomas Haas, Frankfurt (DE); Norbert Finke, Oer-Erkenschwick (DE); Werner Burkhardt, Brachttal (DE); Juergen Grunert, Freigericht (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/449,772

(22) Filed: Jun. 2, 2003

(65) Prior Publication Data

US 2004/0034252 A1    Feb. 19, 2004

(30) Foreign Application Priority Data

May 31, 2002    (EP) ................................. 02012040

(51) Int. Cl.
*B01J 21/18*    (2006.01)
*B01J 23/00*    (2006.01)

(52) U.S. Cl. ............ 502/182; 502/185; 502/325; 502/331; 502/326; 502/332; 502/330; 502/333; 502/334; 502/335; 502/336; 502/337; 502/338; 502/261

(58) Field of Classification Search ............... 502/325, 502/331, 326, 332, 330, 333, 334, 335, 336, 502/337, 338, 182, 185, 261
See application file for complete search history.

(56) References Cited

U.S. PATENT DOCUMENTS

| | | | |
|---|---|---|---|
| 2,606,925 A | 8/1952 | Whitman | |
| 3,155,724 A | 11/1964 | Arthur | |
| 3,347,917 A | 10/1967 | Arthur | |
| 3,914,307 A | 10/1975 | Massie | |
| 5,360,934 A | 11/1994 | Vedage et al. | |
| 5,399,535 A * | 3/1995 | Whitman | 501/80 |
| 6,388,149 B1 * | 5/2002 | Ruhl et al. | 585/254 |
| 6,432,861 B1 * | 8/2002 | Breitscheidel et al. | 502/103 |
| 2004/0097661 A1 * | 5/2004 | Finke et al. | 525/453 |
| 2004/0097752 A1 * | 5/2004 | Lettmann et al. | 560/345 |

FOREIGN PATENT DOCUMENTS

| | | |
|---|---|---|
| EP | 0 066 211 | 12/1982 |
| EP | 0 324 190 | 7/1989 |
| EP | 0 639 403 | 2/1995 |
| EP | 0 813 906 | 12/1997 |
| EP | 0 814 098 | 12/1997 |
| EP | 0 873 300 | 8/2000 |

OTHER PUBLICATIONS

G. F. Allen, Chem Ind., (Dekker), vol. 33, pp. 323-338, "The Hydrogenation of Methylenedianiline", 1988, no month.

* cited by examiner

*Primary Examiner*—Elizabeth D. Wood
(74) *Attorney, Agent, or Firm*—Oblon, Spivak, McClelland, Maier & Neustadt, P.C.

(57) ABSTRACT

The invention relates to a process for hydrogenating an aromatic amine that has at least one amino group bound to an aromatic nucleus with hydrogen in the presence of a supported catalyst that contains at least ruthenium as active metal. The catalyst support has a BET surface area in the range from greater than 30 $m^2/g$ to less than 70 $m^2/g$ and more than 50% of the pore volume of the catalyst support is formed by macropores having a pore diameter of greater than 50 nm and less than 50% are mesopores having a pore diameter of 2 to 50 nm.

9 Claims, No Drawings

PROCESS FOR HYDROGENATING AN AROMATIC AMINE IN THE PRESENCE OF A SUPPORTED RUTHENIUM CATALYST

BACKGROUND OF THE INVENTION

1. Field of the Invention

The invention relates to a process for hydrogenating an aromatic amine that has at least one amino group bound to an aromatic nucleus, wherein the hydrogenation with hydrogen takes place in the presence of a supported catalyst containing ruthenium as an active metal.

2. Discussion of the Background

Cycloaliphatic amines obtained in the catalytic hydrogenation of aromatic amines, such as unsubstituted or substituted cyclohexyl amines and dicyclohexyl amines, are useful in the preparation of polyamide and polyurethane resins, as hardeners for epoxy resins and also as raw materials for the preparation of plastic additives, rubber additives, and corrosion inhibitors.

It is known to prepare cycloaliphatic amines containing one or more amino groups by catalytic hydrogenation of the corresponding mononuclear or polynuclear aromatic amines containing one or more amino groups and optionally further substituents. Such amines are hydrogenated to form the corresponding cycloaliphatic amines, often using supported catalysts.

Thus, in the process described in U.S. Pat. No. 2,606,925, bis(4-aminophenyl)methane (hereinafter, methylenedianiline or MDA) is hydrogenated in the presence of a ruthenium supported catalyst, active carbon, aluminum oxide and kieselguhr as support, to form bis(4-aminocyclohexyl)methane (hereinafter bis(p-aminocyclohexyl)methane or PACM). In this process, PACM takes the form of the cis-cis, cis-trans and trans-trans isomers. Hydrogenation temperatures above 150° C. or prolonged reaction times during the hydration result in an increased proportion of the trans-trans isomers. No indications can be found in U.S. Pat. No. 2,606,925 whether and in what way the selection of the catalyst or catalyst support influences the isomer distribution.

In an effort to obtain the thermodynamically more stable trans-trans isomer of PACM, the hydrogenation described in U.S. Pat. Nos. 3,155,724 and 3,347,917 is performed using a ruthenium supported catalyst in the presence of ammonia. The generic hydrogenation can also be improved, in accordance with U.S. Pat. No. 3,914,307, in that the reaction mixture to be hydrogenated additionally contains a polyheterocyclic amine as cocatalyst. No indications can be found in any of these three patents about the isomeric ratio in the hydrogenation of polynuclear aromatic amines such as MDA to form PACM or any influence of the properties of the support material.

U.S. Pat. No. 5,360,934 discloses a generic method, but a rhodium-containing supported catalyst is used. Ruthenium may also be present as active metal. According to this reference, the catalyst activity depends to an appreciable extent on the modification of the aluminum oxide used as support. According to this reference, catalysts containing delta-, theta- and kapa-aluminum oxide as support material are more active than a catalyst containing commercial gamma-aluminum oxide as support material.

In accordance with EP 0 066 211 A1, dianilinomethane can be converted into PACM having a trans-trans isomeric PACM component in the range from 15 to 40 wt. %, in particular 18.5 to 23.5 wt. % by performing the hydrogenation in the presence of a support-free ruthenium catalyst. This process has the disadvantages of high hydrogenation pressure, high reaction temperature, and the greater effort expended on separating the ruthenium catalyst from the reaction mixture.

In accordance with EP patent 0 324 190, PACM containing the above-mentioned low trans-trans isomeric component can be obtained by hydrogenating MDA in the presence of a support-bound ruthenium catalyst. The hydrogenation takes place at 100 to 190° C. and a pressure of 5 to 35 MPa, in which process, although the temperature was in the lower temperature range in the exemplary embodiments, the hydrogen pressure at 30 MPa was in the upper part of the above-mentioned pressure range. The support material of the catalyst used in this process is characterized by a BET surface area range of 70 to 280 $m^2/g$ and a mean pore diameter $d_p$ of 1 to 32 nm; the penetration depth of the ruthenium is at least 50 µm, in particular 100 to 300 µm; and the ruthenium content is specified as 0.1 to 5 wt. %, in particular 0.5 to 3 wt. %. A disadvantage of this process however is that a high hydrogen hydrogenation pressure is still required in practice.

In accordance with EP 0 813 906 A2, organic compounds, including aromatic compounds in which at least one amino group is bound to an aromatic nucleus, can be hydrogenated using a ruthenium supported catalyst. In addition to ruthenium, the catalyst may contain, as active metal, other metals from the first, seventh or eighth subgroup of the periodic system. In contrast to the support material of EP patent 0 324 190 mentioned above, the support material has, in EP 0813906 A2, a BET surface area of not more than 30 $m^2/g$ and a mean pore diameter of at least 50 nm. The catalyst used in this case is also characterized by a ratio of the surface area of the active metal and the surface area of the catalyst support of less than 0.05. The macroporous support materials having a mean pore diameter of preferably 500 nm to approximately 50 µm are preferably aluminum oxide and zirconium oxide. Details on the hydrogenation of MDA to form PACM are not found in this document, however. In particular, the hydrogenation of aromatic compounds such as 4-alkalyl-substituted phenols results predominantly in trans cycloaliphatic compounds.

A similar process to that of EP 0 813 906 A2 is disclosed in EP 0 814 098 A2: the support materials for the support-bound ruthenium hydrogenation catalysts for hydrogenating aromatic amines to cycloaliphatic amines are those materials in which 10 to 50% of the pore volume is formed by macropores having a pore diameter in the range from 50 nm to 10,000 nm and 50 to 90% is formed by mesopores having a pore diameter in the range from 2 to 50 nm. The BET surface area of the support is specified as 50 to 500 $m^2/g$, in particular 200 to 350 $m^2/g$. The ratio of the surface of the active metal and of the support is said to be less than 0.3, in particular less than 0.1. Neither the activity of such catalysts nor the isomeric ratio in the case of the hydrogenation of MDA to form PACM are described in this reference. However, reference is also made here to the predominant formation of the trans isomers with reference to the hydrogenation of 4-substituted phenols.

EP 0 873 300 B1 proposes carrying out the hydrogenation of aromatic amines such as bis(p-aminophenyl)methane, with a catalyst containing support-bound ruthenium as active metal, the support having a mean pore diameter of at least 0.1 µm, in particular at least 0.5 µm and a surface area of not more than 15 $m^2/g$, preferably 0.05 to 5 $m^2/g$. Cycloaliphatic amines can be obtained by this process with high selectivity and without the formation of deamination products or partially hydrogenated dimerization products. Trans-trans isomeric components are not disclosed.

As is disclosed by G. F. Allen (Chem. Ind. (Dekker) (1988), 33 Catal. Org. Reakt., 323–338), the trans-trans isomeric PACM component increases with increasing conversion of metylhenediamine. The two above-mentioned processes relate, however, only to obtaining a high conversion.

EP 0 639 403 A2 discloses that bis(p-aminocyclohexyl)methane can be produced by hydrogenation of methylenedianiline with a ruthenium-containing or rhodium-containing supported catalyst, the layer thickness of the active metals on the support being 5 to 150 μm, preferably 10 to 80 μm. The support material is a calcined and superficially rehydrated transition argillaceous earth having a specified pH. The support has a BET surface area of at least 70 m$^2$/g and an open porosity of at least 0.1 ml/g. Pore distribution is not disclosed. An advantage of this process is that, even after a prolonged operating time, the proportion of trans-trans PACM isomer is in the range from about 20 to 25%. Disadvantages of this process are, however, the increased effort in establishing an equilibrium pH, the high expenditure on equipment required to apply the high hydrogen pressure (300 bar) mentioned in the examples, and the limited selection of supports.

In accordance with the process disclosed in DE 199 42 813, PACM with a low trans-trans isomer component can be obtained in an advantageous way at a moderate temperature of 50 to below 130° C. and a moderate hydrogen pressure of 3 to 10 MPa using a ruthenium supported catalyst bound to titanium dioxide or aluminum oxide. The specific surface area of the titanium dioxide used particularly preferably is in the range from greater than 20 m$^2$/g to less than 70 m$^2$/g. A disadvantage of this process, however, is the high ruthenium content of the supported catalyst required. Pore structure/distribution is not disclosed.

SUMMARY OF THE INVENTION

One object of the present invention is to provide a process for the hydrogenation of aromatic amines in the presence of a ruthenium-containing supported catalyst by which desired cycloaliphatic amines can be obtained with higher selectivity.

Another object of the invention provides a process for preparing bis(p-aminocyclohexyl)methane by catalytic hydrogenation of methylenedianiline, in which process the trans-trans isomeric component of the PACM should be less than 30%, in particular 15 to 25%.

Another object is to obtain a low trans-trans component and a high conversion.

Another object is that the catalyst used in the process should have a long working life and the isomer distribution should remain substantially unaltered even after a prolonged operating time.

These and other objects are achieved by the invention, the first embodiment of which provides a process for hydrogenating an aromatic amine that having at least one amino group bound to an aromatic nucleus, which includes:

reacting the aromatic amine with hydrogen in the presence of a supported catalyst;

wherein the catalyst includes as active metal ruthenium alone or together with at least one metal selected from the group including the first, seventh or eighth subgroups of the periodic system in an amount of 0.01 to 20 wt % of active metals, based on the supported catalyst, and a support, wherein the support has a BET surface area ranging from greater than 30 m$^2$/g to less than 70 m$^2$/g, and wherein more than 50% of the pore volume of the support are macropores having a pore diameter of greater than 50 nm, and less than 50% of the pore volume of the support are mesopores having a pore diameter of 2 to 50 nm, to obtain a hydrogenated aromatic amine.

Another embodiment of the invention provides a supported catalyst which includes, as active metal, ruthenium alone or together with at least one metal selected from the group including the first, seventh or eighth subgroup of the periodic system in an amount of 0.01 to 20 wt % of active metals, based on the supported catalyst, and a support, wherein the catalyst support has a BET surface area ranging from greater than 30 m$^2$/g to less than 70 m$^2$/g and more than 50% of the pore volume of the catalyst support are macropores having a pore diameter of greater than 50 nm and less than 50% are mesopores having a pore diameter of 2 to 50 nm.

Another embodiment provides a process for making the above catalyst, which includes applying an active metal(s) to a support by spraying the support with at least one dilute active metal salt solution at a temperature of at least 80° C. and then drying.

DESCRIPTION OF THE PREFERRED EMBODIMENTS

A more complete appreciation of the invention and many of the attendant advantages thereof will be readily obtained as the same becomes better understood by reference to the following detailed description.

The process preferably includes hydrogenating an aromatic amine that has at least one amino group bound to an aromatic nucleus, which includes reaction of the aromatic amine with hydrogen in the presence of a supported catalyst containing ruthenium alone as the active metal or together with at least one metal of the first, seventh or eighth subgroups of the periodic system in an amount of 0.01 to 20 wt. %, in particular 0.2 to 3 wt. % of active metals, based on the supported catalyst, applied to a support, characterized in that the catalyst support has a BET surface area in the range from greater than 30 m$^2$/g to less than 70 m$^2$/g and more than 50% of the pore volume of the catalyst support are macropores having a pore diameter of greater than 50 nm and less than 50% are mesopores having a pore diameter of 2 to 50 nm.

In regard to the references discussed in detail above, in particular to EP 0 814 098 A2, it is surprising that a catalyst support having a specific surface area in the range from greater than 30 m$^2$/g to less than 70 m$^2$/g is particularly effective in the generic process if more than 50% of the pore volume is formed by macropores and less than 50% of the pore volume is formed by mesopores. Without wishing to be bound by theory, it is believed that not the BET surface area alone or the pore distribution alone that is important, but the combination of these two features. The inventive combination of properties of the support material is also surprising because, in EP 0 324 190 B considered above, for a BET surface area of at least 70 m$^2$/g, the pore volume should substantially be formed exclusively by mesopores having a mean pore diameter of 1 to 32 nm. Finally, the catalyst used in the process in accordance with the present invention differs in a fundamental way from the catalyst disclosed in EP 0 813 906 A2 because, although the catalyst support in the predisclosed process is macroporous, the BET surface area should, however, be not more than 30 m$^2$/g and preferably not more than 15 m$^2$/g. The ratio of the surface area of the active metal and of the catalyst support is in the range from 0.01 to 0.5, in particular 0.03 to 0.3. Surprisingly, a low surface area ratio of the active metal, determined by CO chemisorption, and of the catalyst support, determined by BET, of 0.03 to 0.06 in the case of the catalyst to be used according to the invention also results in a high catalyst activity under mild hydrogenation conditions.

Aromatic amines in which at least one amino group is bound to an aromatic nucleus can be hydrogenated to form the corresponding cycloaliphatic compounds by the process according to the invention. The aromatic compounds may be mononuclear or polynuclear aromatic compounds. Preferably, the aromatic compounds are aromatic amines or diamines or triamines. The aromatic amines may be substituted on the aromatic nucleus or nuclei or/and on the amino group, for example by one or more alkyl and/or alkoxy radicals, preferably $C_{1-20}$-alkyl and/or $C_{1-20}$-alkoxy radicals. Particularly preferred substituents are $C_{1-10}$-alkyl radicals, in particular methyl, ethyl, propyl, isopropyl, butyl, isobutyl, tert-butyl radicals. Among the alkoxy radicals, the $C_{1-8}$-alkoxy radicals, in particular methoxy, ethoxy, propoxy and butoxy, are preferred. The aromatic nucleus or nuclei and also the alkyl and alkoxy radicals may optionally be substituted by halogen atoms, in particular fluorine atoms or other suitable inert or hydrogenable substituents.

Preferably, the substituted aromatic amines are converted into cycloaliphatic amines having a low trans component.

Preferably, in the process for preparing bis(p-aminocyclohexyl) methane by catalytic hydrogenation of methylenedianiline, the trans-trans isomeric component of the PACM is less than 30%, more preferably 15 to 25%. These ranges expressly include 29, 27, 23, 21, 17, 13, 11, 9, 7, and 5%.

Preferably, the aromatic amine (and most preferably the MDA) conversion is greater than 80%, which range includes 82, 84, 86, 88, 90, 91, 92, 93, 94, 95, 96, 97, 98, 99, 99.9, and 100%.

The aromatic amine in which at least one amino group is bound to an aromatic nucleus may also have a plurality of aromatic nuclei that are linked by means of a bivalent hydrocarbon radical, such as a methylene group or ethylene group. The linking radical may have one or more alkyl substituents, in particular $C_{1-20}$-alkyl radicals, preferably one or more methyl, ethyl, n-propyl or isopropyl, n-butyl or sec-butyl or tert-butyl radicals.

Particularly preferred aromatic amines are aniline, naphthylamine, bis(p-aminophenyl)methane, and also isomers thereof, that is to say 2,4'- and 2,2'-diaminodiphenylmethane, bis(p-aminophenyl)amines, 2,2-bis(p-aminophenyl)propane, in which case one or both aromatic nuclei may have a further amino group and/or a $C_1$- to $C_3$-alkyl or alkoxy group.

The above carbon ranges includes any and all subranges therebetween, including 1, 2, 3, 4, 5, 6, 7, 8, 9, 10, 11, 12, 13, 14, 15, 16, 17, 18, 19, and 20 carbons as appropriate.

The supported catalysts used according to the invention can be prepared industrially by applying ruthenium and optionally at least one metal of the first, seventh or eighth subgroup to a suitable support. Mixtures of metals are possible. The application can be achieved by impregnating the support in aqueous metal salt solutions, such as ruthenium salt solutions, by spraying suitable metal salt solutions onto the support or by other suitable processes. Preferred salts for preparing the ruthenium salt solutions and also solutions of metal salts of elements of the first, seventh or eighth subgroup include the nitrates, nitrosyl nitrates, halides, carbonates, carboxylates, acetylacetonates, chlorine complexes, nitro complexes or amine complexes of the corresponding metals; preferred are nitrates and nitrosyl nitrates. Mixtures of salts are possible.

In the case of catalysts that contain one or more other metals in addition to ruthenium applied to the support, the metal salts or metal salt solutions can be applied simultaneously or consecutively.

The periodic system described herein is preferably referenced in the "Handbook of Chemistry and Physics," $66^{th}$ edition, 1985–1986, CRC Press, the entire contents of which is hereby incorporated by reference. The first, seventh and eighth subgroup elements include one or more elements selected from the group including Cu, Ag, Au, Mn, Re, Fe, Co, Ni, Rh, Pd, Os, Ir, Pt, and any combination thereof.

The supports coated or impregnated with a ruthenium salt or additionally further metal salt solutions are dried, preferably at temperatures between 100° C. and 150° C., and optionally calcined at temperatures between 200° C. and 600° C. The coated supports are then activated by treating the coated supports in a gas stream containing free hydrogen at temperatures between 30 and 600° C., preferably between 150 and 400° C. The gas stream is preferably composed of 50 to 100 vol. % of $H_2$ and 0 to 50 vol. % of $N_2$.

If one or more other metals of the first, seventh or eighth subgroup are applied to the supports in addition to ruthenium, and the application takes place consecutively, the support may be dried after every application or impregnation at temperatures between 100 and 150° C. and optionally calcined at temperatures between 200 and 600° C. In this connection, the order in which the metal salt solutions are applied may be chosen as desired.

The ranges above include all values and subranges therebetween, including: (for drying temperatures) 100, 105, 110, 115, 120, 125, 130, 135, 140, 145 and 150° C.; (for calcining temperatures) 200, 225, 250, 275, 300, 350, 375, 400, 425, 450, 475, 500, 525, 550, 575 and 600° C.; (for activating temperatures) 30, 60, 90, 100, 150, 200, 250, 300, 350, 400, 450, 500, 550, and 600° C.; (for $H_2$ in gas stream) 50, 55, 60, 65, 70, 75, 80, 85, 90, 95 and 100 vol %; and (for $N_2$ in gas stream) 0, 5, 10, 15, 20, 25, 30, 35, 40, 45 and 50 vol %.

Preferably, the support is coated by spraying a metal salt solution thereon at elevated temperature, in particular above 50° C. and, particularly preferably, at or above 80 to 150° C. so that the solvent is at least partly evaporated even during the coating and the penetration depth of the catalytically active metal is limited. These ranges include all values and subranges therebetween, including at or above 51, 55, 60, 65, 70, 75, 80, 85, 90, 100, 110, 120, 130, 140 and 150° C. Preferably, the penetration depth is in the range from 5 to 250 μm, in particular 10 to 150 μm and, particularly preferably, 50 to 120 μm. These ranges include all values and subranges between including 5, 10, 15, 25, 50, 75, 100, 150, 200, 225, and 250 μm.

The ruthenium salt solution and, optionally, one or more additional metal salt solutions are applied to the support or supports in an amount such that 0.01 to 20 wt. %, based on the total weight of the supported catalyst (=total weight of support material(s) plus active metal(s)), of ruthenium and, optionally, other metals of the first, seventh or eighth subgroup are applied to the support. Preferably, the amount of active metal is 0.2 to 15 wt. %, in particular about 0.2 to 3 wt. %, the ruthenium content preferably exceeding the content of the other metals. These ranges include all values and subranges therebetween, including 0.01, 0.02, 0.05, 0.07, 0.1, 0.3, 0.5, 0.7, 0.9, 1, 5, 10, 15 and 20 wt. %.

The support materials of the catalysts to be used according to the invention have a specific BET surface area (determined with $N_2$ in accordance with DIN 66131, incorporated herein by reference) in the range from greater than 30 m²/g and less than 70 m²/g. These ranges include all values and subranges therebetween, including 31, 33, 35, 37, 39, 40, 43, 45, 47, 50, 55, 60, 61, 62, 65, 67 and 69 m²/g.

The support contains macropores having a pore diameter of greater than 50 nm. The diameter of the macropores is, in particular, in the range from 50 to 50,000 nm, in many cases, however, in the range from 50 to 10,000 nm. The support may also contain mesopores. If the support also comprises mesopores, these are understood to be pores in the range from 2 to 50 nm.

The above macropore pore diameter ranges expressly include 50, 51, 55, 60, 70, 80, 90, 100, 250, 500, 750, 1000, 10,000, 20,000, 30,000, 40,000, 50,000 and greater than 50,000 nm. The above mesopore pore diameter ranges expressly include 2, 3, 5, 7, 9, 10, 15, 20, 25, 30, 35, 40, 45, 47, 49, less than 50, and 50 nm.

At least 50% of the pore volume is formed by macropores and less than 50% by mesopores. Preferred supports contain macropores in an amount of 55 to 85% of the pore volume and 15 to 45% of the pore volume is occupied by mesopores. In particularly preferred supports, mesopores occupy about 25 to 45% of the pore volume and macropores the rest of the pore volume. If present, micropores having a pore diameter of less than 2 nm are present only in an amount of less than 10% of the pore volume, in particular less than 1%.

The above pore volume ranges formed by macropores expressly include 50, 51, 53, 55, 57, 59, 60, 69, 70, 75, 80, 90, 95, 99, less than 100, and 100%. The above pore volume ranges formed by mesopores expressly include 0, greater than 0, 1, 3, 5, 7, 9, 10, 15, 20, 25, 30, 35, 40, 45, 47, 49 and less than 50%. The above pore volume ranges formed by micropores expressly includes 0, 0.5, 1, 2, 3, 4, 5, 6, 7, 9 and less than 10%.

The modification of the support may be uniform or mixed so that the pore distribution may be monomodal, bimodal or trimodal.

All the known support materials can be used for hydrogenation catalysts provided they have the required BET surface, pore size and pore distribution. Oxidic, silicatic and nitridic supports are suitable and, in particular, those have a single-phase or multiphase crystalline or X-ray amorphous or mixed structure.

The supports may additionally be modified in a known way with alkali-metal or/and alkaline-earth-metal compounds and/or with metals of the lanthanide series.

Exemplary supports are oxides from the series comprising $Al_2O_3$, $TiO_2$, $ZrO_2$, $SiO_2$, MgO and ZnO, mixed oxides such as spinels, for example $MgAl_2O_4$. Aluminum silicates and active carbons are also suitable if these supports have the claimed combination of properties. Particularly preferred are the oxides $Al_2O_3$ and $TiO_2$. Mixtures are possible.

The hydrogenation is preferably performed at a temperature in the range from 20 to 250° C., in particular at below 200° C., and an effective $H_2$ partial pressure in the range from about 1 to 30 MPa, preferably below 10 MPa, in a continuously operated or batch-operated suspension-type or fixed-bed hydrogenation reactor.

The above hydrogenation temperature ranges expressly include 20, 22, 25, 27, 30, 35, 45, 55, 65, 75, 100, 150, 175, 200, 225 and 250° C. The above effective $H_2$ partial pressure range expressly includes 1, 3, 5, 7, 9, 10, 15, 20, 25, and 30 MPa.

The activity of the catalysts according to the invention make it possible to perform the hydrogenation under mild conditions, preferably at a temperature in the range from 50 to 150° C., in particular 70 to 120° C. and an $H_2$ pressure in the range from 3 to 10 MPa, with the result that industrially less expensive reactors can be used, which increases the cost-effectiveness of the process.

The hydrogenation can be performed in the presence or absence of a suitable solvent. Preferably, a solvent is present and, more preferably, in an amount of about 10 to 90 wt. %, based on the solution of the aromatic amine to be hydrogenated. This range expressly includes about 10, 20, 30, 40, 50, 60, 70, 80, 90 and about 90 wt. %.

Suitable solvents include, for example, primary, secondary and tertiary monohydric or polyhydric alcohols, such as methanol, ethanol, n-propanol and isopropanol, n-, sec-, and tert-butanol, ethylene glycol, ethylene glycolmono($C_1$–$C_4$) alkyl ethers; linear ethers, such as ethylene glycol di($C_1$–$C_3$) alkyl ethers; cyclic ethers, such as tetrahydrofuran and dioxane; alkanes, such as n-alkanes and isoalkanes containing 4 to 12 C atoms, for example n-pentane, n-hexane and isooctane, and cyclic alkanes, such as cyclohexane and decalin. Mixtures are possible.

The hydrogenation can also be performed in the presence of ammonia or a primary, secondary or tertiary amine or a polycyclic amine having a bridged N atom. Preferably, no undesirable isomerization occurs among those chosen in the case of PACM, i.e., in the direction of a higher trans-trans component.

One preferred embodiment of the invention relates particularly to a process for hydrogenating methylenedianiline (MDA) to form bis(p-aminocyclohexyl)methane (PACM) having a content of the trans-trans isomers thereof in the range of, in particular, 15 to 25%.

The solvent may also be or include the hydrogenation product itself, for example, a cycloaliphatic amine.

For continuous hydrogenation, a fixed-bed reactor is preferred. The fixed-bed reactor can be operated as a bubble or trickle-bed reactor but a trickle-bed mode is preferred. Preferably, a trickle-bed reactor having an LHSV value in the range from 0.1 to 5 h$^{-1}$ (=1 of the aromatic amines to be hydrogenated per 1 fixed bed catalyst and hour). In accordance with a particularly preferred embodiment of the process according to the invention, a multitube fixed-bed reactor is used and it is operated in the trickle-bed mode. The LHSV value includes 0.1, 0.2, 0.5, 0.7, 1, 2, 2, 5, 3, 4, 4, 5, and 5h$^{-1}$.

Preferably, the supported catalyst contains, as active metal, ruthenium alone or together with at least one metal of the first, seventh or eighth subgroup of the periodic system in an amount of 0.01 to 20 wt. % of active metals, based on the supported catalyst for the purpose of hydrogenating an aromatic amine that has at least one amino group bound to an aromatic nucleus, characterized in that the catalyst support has a BET surface area in the range from greater than 30 m²/g to less than 70 m²/g and more than 50% of the pore volume of the catalyst support is macropores having a pore diameter of greater than 50 nm and less than 50% are mesopores having a pore diameter of 2 to 50 nm.

The catalyst can be used for other hydrogenations, for example the hydrogenation of phenols and nitrites. Preferably, the amount of ruthenium exceeds the amount of the other active metals. Preferably, the catalyst contains 0.2 to 3 wt. % of active metals, wherein at least 90% is, in particular, ruthenium.

The hydrogenated aromatic amines prepared in accordance with the invention and, more preferably, the cycloaliphatic amines, may be further utilized in the preparation of other useful products without departing from the scope of the present invention. These products include but are not limited to polyamide and/or polyurethane resins (in the latter case, the isocyanate of the cycloaliphatic amine is preferably used), isocyanates, epoxy resins, plastic and/or rubber additives, and corrosion inhibitors.

Other preferred embodiments A–J are listed below:

A. A process for hydrogenating an aromatic amine that has at least one amino group bound to an aromatic nucleus, comprising reaction of the aromatic amine with hydrogen in the presence of a supported catalyst containing ruthenium alone as active metal or together with at least one metal of the first, seventh or eighth subgroups of the periodic system in an amount of 0.01 to 20 wt % of active metals, based on the supported catalyst, applied to a support, characterized in that the catalyst support has a BET surface area in the range from greater than 30 $m^2/g$ to less than 70 $m^2/g$ and more than 50% of the pore volume of the catalyst support are macropores having a pore diameter of greater than 50 nm and less than 50% are mesopores having a pore diameter of 2 to 50 nm.

B. Process according to preferred embodiment A, characterized in that the active metal applied to the catalyst has a penetration depth into the support in the range of 20 to 500 μm, in particular 25 to 250 μm.

C. Process according to preferred embodiments A or B, characterized in that the ratio of the surfaces of the active metal, determined by CO pulse chemisorption, and of the catalyst support, determined by BET, is greater than 0.01, in particular 0.03 to 0.3.

D. Process according to any of preferred embodiments A to C, characterized in that the support material is selected from the series comprising crystalline and amorphous oxides and silicates, in particular selected from the series comprising $Al_2O_3$, $SiO_2$, $TiO_2$, $ZrO_2$, MgO, ZnO and aluminosilicates.

E. Process according to any of preferred embodiments A to D, characterized in that the catalyst support has a BET surface in the range from 32 to 67 $m^2/g$, the penetration depth of the active metals is in the range from 50 to 200 μm and the amount of Ru is in the range from 0.2 to 3 wt. %, based on the catalyst, and at least 55% of the pore volume of the catalyst support is formed by macropores and less than 45% by mesopores.

F. Method according to any of preferred embodiments A to E, characterized in that a 4,4'-diaminodiphenyl($C_1$ to $C_4$)alkane and/or a 2,4'-oder 2,2' isomer thereof, in particular 4,4'-diaminodiphenylmethane or an isomer thereof is hydrogenated.

G. Process according to any of preferred embodiments A to F, characterized in that the hydrogenation is performed at a temperature in the range from 20 to 200° C., in particular 50 to 150° C., and a hydrogen partial pressure in the range from 3 to 30 MPa, in particular 3 to 10 MPa.

H. Process according to any of preferred embodiments A to G, characterized in that the hydrogenation is performed in a fixed-bed reactor, in particular in a multitube fixed-bed reactor, in the trickle-bed mode.

I. Process according to any of preferred embodiments A to H, characterized in that a supported catalyst is used whose active metal ruthenium was applied to a support by spraying the support with a dilute ruthenium salt solution, in particular a ruthenium nitrosyl nitrate solution at a temperature of at least 80° C. and then drying.

J. Supported catalyst that contains, as active metal, ruthenium alone or together with at least one metal of the first, seventh or eighth subgroup of the periodic system in an amount of 0.01 to 20 wt % of active metals, based on the supported catalyst applied to a support for the purpose of hydrogenating an aromatic amine that has at least one amino group bound to an aromatic nucleus, characterized in that the catalyst support has a BET surface area in the range from greater than 30 $m^2/g$ to less than 70 $m^2/g$ and more than 50% of the pore volume of the catalyst support are macropores having a pore diameter of greater than 50 nm and less than 50% are mesopores having a pore diameter of 2 to 50 nm.

EXAMPLES

Having generally described this invention, a further understanding can be obtained by reference to certain specific examples which are provided herein for purposes of illustration only and are not intended to be limiting unless otherwise specified.

Preparation of the Catalyst:

Example 1

An aluminum oxide moulding (extrudate, d=3 mm) having a BET surface area of approximately 33 $m^2/g$ and a bimodal pore distribution having a pore volume of 0.41 ml/g, in which substantially no pores were found that had a diameter of 2 to 50 nm, but 100% of the pore volume comprised macropores having a diameter in the range from 50 to 10,000 nm, was coated with an aqueous ruthenium(III) nitrate solution at approximately 90 to 100° C. by spraying the catalyst solution onto the moving support material, in which process water simultaneously evaporated. The catalyst solution had a concentration of 5% metal, based on the weight of the solution. The support coated in this way was heated at a temperature of 120 to 180° C. and then reduced with a mixture of 50% $H_2$ and 50% $N_2$ at 200° C. for 4 h. The catalyst prepared in this way contained 3 wt. % ruthenium, based on the total weight of the catalyst. The ruthenium penetration depth was 70–90 μm. The ratio of the ruthenium surface determined by CO chemisorption to the surface of the uncoated support material determined by BET was about 0.05. The aluminum oxide moulding was substantially composed of alpha- and gamma-$Al_2O_3$ (approximately 18 wt. % $SiO_2$ and approximately 2 wt. % alkali-metal and alkaline-earth oxides, $Fe_2O_3$ and $Ti_2O$.

Example 2

An aluminum oxide moulding (extrudate, d=3 mm) of similar composition to that of the support in Example 1 having a BET surface area of approximately 32 $m^2/g$, trimodal pore distribution and a pore volume of 0.58 ml/g was impregnated analagously as in Example 1. The pore volume of the support material resulted from 31% pores having a pore diameter of from 2 to 50 nm, 44% pores 50 to 10,000 nm and 25% pores having a pore diameter of greater than 10,000 nm to 5 μm. The catalyst prepared in this way contained, as Example in 1, 3 wt. % ruthenium and the penetration depth was 70 to 90 μm.

Example 3

An aluminum oxide moulding (extrudate, d=3 mm) having a surface area of approximately 54 $m^2/g$ had, with a trimodal pore distribution, a pore volume of 0.77 ml/g. 40% of the pore volume resulted from pores having a diameter of 2 to 50 nm, 60% of pores having a pore diameter of 50 to 10,000 nm. The impregnation of the support, and calcination and reduction of the catalyst took place in the same way as in Example 1. The catalyst prepared in this way contained 3 wt. % ruthenium, based on the total weight of the catalyst. The penetration depth was 70 to 90 μm. The aluminum oxide moulding used comprised the alpha-, theta- and gamma-$Al_2O_3$ modifications.

Example 4

An aluminum oxide moulding composed of spheres having a diameter of 2–4 mm and having a BET surface area of approximately 35 m$^2$/g had, with a monomodal pore distribution, a pore volume of 0.5 ml/g. 42% of the pore volume was formed by mesopores (2 to 50 nm) and 58% by macropores (50 to 10,000 nm). The support material comprised the theta- and gamma-Al$_2$O$_3$ modifications. The impregnation, calcining and reduction took place in the same way as in Example 1. The support-bound ruthenium catalyst obtained in this way contained 3 wt. % ruthenium, based on the total weight of the catalyst. The ruthenium penetration depth was 80 to 120 μm.

Comparison Example 1

A titanium dioxide moulding (extrudate, d=2 mm) substantially composed of a mixture of rutile and anatase having a BET surface area of 45 m$^2$/g had, with a monomodal pore distribution, a pore volume of 0.35 ml/g. The pore volume was formed by 100% of mesopores (2 to 50 nm). The moulding was impregnated analogously as in Example 1, but the drying took place at 150 to 160° C. and the subsequent reduction took place at 180° C. within 4 h. The catalyst prepared in this way contained 3 wt. % ruthenium, based on the total weight of the catalyst. The penetration depth was 90 to 120 μm.

Comparison Example 2

An aluminum oxide moulding (extrudate, d=1.2 mm) composed substantially of gamma-Al$_2$O$_3$ having a BET surface area of 220 m$^2$/g had a pore volume of 0.65 ml/g, where 95% of the pore volume was formed by mesopores (2 to 50 nm) and 5% of the pore volume was formed by macropores (50 to 10,000 nm). The support was impregnated with an aqueous ruthenium (III) nitrate solution at room temperature. The catalyst solution had a concentration of 5% metal, based on the weight of the solution. The impregnated support was heated at a temperature of 150 to 160° C. and then reduced with a mixture of 50% H$_2$ and 50% N$_2$ at 180° C. for 4 h. The catalyst prepared in this way contained 5 wt. % of ruthenium, based on the total weight of the catalyst. The penetration depth was 600 μm.

Performance of the Hydrogenation Reaction

Examples 5 to 8 and Comparison Examples 3 and 4

In each case, 30 ml of a ruthenium supported catalyst in accordance with one of Examples 1 to 4 or Comparison Examples 1 to 2 were loaded into a tubular reactor heated by an external jacket; the reactor was equipped with a precipitation device. The fixed-bed reactor was first subjected to hydrogen at 90° C. and then loaded with a solution composed of 20 vol % of 4,4'-methylenedianiline and 80 vol % tetrahydrofuran. Hydrogenation was carried out at a hydrogen partial pressure of 8 MPa. The catalyst loading during this trickle-bed procedure was 0.43 [h$^{-1}$]. During the trickling, the temperature was raised to 110° C.

The table below shows operating data and results, including the reaction temperature, the use of a catalyst according to the invention or not according to the invention, the 4,4'-methylenedianiline (MDA) conversion, the MDA conversion per g Ru/h, and also the content of the trans-trans isomeric component. The percentages relate to area percentages determined by gas chromatography.

The extraordinary activity of the Ru supported catalysts to be used according to the invention emerges from the results of the examples according to the invention. If the catalysts according to the invention are used, PACM is produced that has a trans-trans isomeric component in the range of about 15–25%.

TABLE

| Ex. No. | Catalyst | Hydrogenation temperature (° C.) | MDA conversion (%) | % MDA conversion/ g Ru · h | g PACM/g Ru · h | PACM trans-trans-isomers (%) |
|---|---|---|---|---|---|---|
| E 5/1 | E 1 | 102 | 97.4 | 170 | 3.3 | 18 |
| /2 | E 1 | 105 | 99.4 | 174 | 3.5 | 20 |
| /3 | E 1 | 110 | 99.8 | 175 | 3.6 | 25 |
| E 6/1 | E 2 | 94 | 99.8 | 169 | 3.0 | 15 |
| /2 | E 2 | 102 | 100 | 170 | 3.7 | 21 |
| E 7 | E 3 | 100 | 99 | 184 | 4.5 | 16 |
| E 8/1 | E 4 | 98 | 94.2 | 149 | 3.9 | 22 |
| CE 3/1 | CE 1 | 100 | 96.3 | 113 | 2.0 | 22 |
| /2 | CE 1 | 105 | 98.4 | 115 | 2.3 | 25 |
| CE 4 | CE 2 | 94 | 93 | 89 | 1.8 | 20 |

This application is based on European Patent Application No. 02012040.8, filed May 31, 2002, the entire contents of which are hereby incorporated by reference.

Having now fully described the invention, it will be apparent to one of ordinary skill in the art that many changes and modifications can be made thereto without departing from the spirit or scope of the invention as set forth herein.

The invention claimed is:

1. A supported catalyst comprising, as active metal, ruthenium alone or together with at least one metal selected from the group consisting of the first, seventh or eighth subgroup of the periodic system in an amount of 0.01 to 20 wt % of active metal, based on the supported catalyst, and a support, support, selected from the group consisting of Al$_2$O$_3$, TiO$_2$, ZrO$_2$SiO$_2$MgO, ZnO, spinels, aluminium silicates and active carbons and mixtures thereof, wherein the support has a BET surface area ranging from 32 m$_2$/g to 67 m$_2$/g, and wherein at least 55% of the pore volume of the catalyst support are macropores having a pore diameter of greater than 50 nm and less than 45% are mesopores having a pore diameter of 2 to 50 nm.

2. A process for preparing the catalyst claimed in claim 1, comprising applying the active metal to the support by spraying the support with at least one dilute salt solution of the active metal at a temperature of at least 80° C. and then drying the material obtained.

3. The supported catalyst according to claim 1, wherein the active metal has a penetration depth into the support in the range of 5 to 250 μm.

4. The supported catalyst according to claim 3, wherein the active metal has a penetration depth into the support in the range of 50 to 120 μm.

5. The supported catalyst according to claim 1, wherein the ratio of the surface area of the active metal, determined by CO pulse chemisorption, and of the support, determined by BET, is in the range from 0.01 to 0.5.

6. The supported catalyst according to claim 5, wherein the ratio of the surface area of the active metal, determined by CO pulse chemisorption, and of the support, determined by BET, is in the range from 0.03 to 0.06.

7. The supported catalyst according to claim 1, wherein the penetration depth of the active metal in the support is in the range from 50 to 200 μm and wherein ruthenium is present in an amount m the range of 0.2 to 3 wt. %, based on the supported catalyst.

8. The supported catalyst according to claim 1, wherein from 55 to 85% of the pore volume of the support is formed by macropores.

9. The supported catalyst according to claim 1, wherein from 25 to 45 % of the pore volume of the support is formed by mesopores.

* * * * *

UNITED STATES PATENT AND TRADEMARK OFFICE
CERTIFICATE OF CORRECTION

PATENT NO. : 7,030,052 B2
APPLICATION NO. : 10/449772
DATED : April 18, 2006
INVENTOR(S) : Guido Stochniol et al.

It is certified that error appears in the above-identified patent and that said Letters Patent is hereby corrected as shown below:

Column 12, line 54-55, "and a support, support, selected", should read -- and a support, selected --;

Column 12, line 56, "$ZrO_2SiO_2Mgo$", should read -- $ZrO_2$, $SiO_2$, $MgO$ --;

Column 12, line 58, "32 $m_2$/g to 67 $m_2$/g", should read -- 32 $m^2$/g to 67 $m^2$/g --.

Signed and Sealed this
Second Day of October, 2012

David J. Kappos
*Director of the United States Patent and Trademark Office*